(12) United States Patent
Fridman et al.

(10) Patent No.: US 7,491,860 B2
(45) Date of Patent: Feb. 17, 2009

(54) DEHYDROGENATION PROCESS

(75) Inventors: Vladimir Fridman, Louisville, KY (US); Michael Urbancic, Louisville, KY (US); Andrzej Rokicki, Mountain Lakes, NJ (US)

(73) Assignee: Süd-Chemie Inc., Louisville, KY (US)

( * ) Notice: Subject to any disclaimer, the term of this patent is extended or adjusted under 35 U.S.C. 154(b) by 548 days.

(21) Appl. No.: 11/196,033

(22) Filed: Aug. 3, 2005

(65) Prior Publication Data

US 2007/0032691 A1 Feb. 8, 2007

(51) Int. Cl.
*C07C 5/333* (2006.01)
*B01J 23/00* (2006.01)
*C10G 35/04* (2006.01)

(52) U.S. Cl. ............... 585/663; 585/660; 585/662; 502/305; 502/319; 502/320; 502/355; 208/134

(58) Field of Classification Search .......... 585/660, 585/662, 663; 208/133, 134; 502/305, 319, 502/320, 355
See application file for complete search history.

(56) References Cited

U.S. PATENT DOCUMENTS

| | | | |
|---|---|---|---|
| 2,184,235 A | 12/1939 | Groll | |
| 2,300,971 A | 11/1942 | Roberts | |
| 2,328,234 A | 8/1943 | Seguy | |
| 2,419,997 A | 5/1947 | Houdry | |
| 2,485,906 A | 10/1949 | Mills, Jr. | |
| 2,831,041 A * | 4/1958 | Sieg et al. ............... | 585/624 |
| 3,223,743 A | 12/1965 | MacFarlane | |
| 3,363,023 A | 1/1968 | Mooi | |
| 3,620,685 A | 11/1971 | Rogers | |
| 3,904,703 A | 9/1975 | Lo | |
| 3,907,919 A | 9/1975 | Lo | |
| 4,704,497 A | 11/1987 | Gottlieb | |
| 4,739,124 A * | 4/1988 | Ward ............... | 585/658 |
| 5,219,816 A | 6/1993 | Zhou | |
| 5,258,349 A | 11/1993 | Dalla Betta | |
| 5,346,871 A | 9/1994 | Robbins | |
| 5,439,859 A | 8/1995 | Durante | |
| 5,476,982 A | 12/1995 | Robbins | |
| 5,510,557 A | 4/1996 | Gartside | |
| 5,733,518 A | 3/1998 | Durante | |
| 6,544,439 B1 | 4/2003 | Lewis | |
| 7,244,868 B2 * | 7/2007 | Wambaugh ............... | 585/441 |
| 2002/0198428 A1 | 12/2002 | Iezzi | |
| 2004/0087825 A1 | 5/2004 | Urbancic | |

FOREIGN PATENT DOCUMENTS

| | | |
|---|---|---|
| GB | 2 162 082 | 1/1986 |
| WO | WO 95/23123 | 8/1995 |
| WO | WO 2006/124145 | 11/2006 |

* cited by examiner

*Primary Examiner*—Glenn Caldarola
*Assistant Examiner*—In Suk Bullock
(74) *Attorney, Agent, or Firm*—Scott R. Cox

(57) ABSTRACT

A process for adiabatic, non-oxidative dehydrogenation of hydrocarbons including passing a hydrocarbon feed stream through a catalyst bed, wherein the catalyst bed includes a first layer of a catalyst and second layer of a catalyst, wherein the catalyst of the first layer has high activity but a higher capacity for producing coke than the catalyst of the second layer and the second catalyst also has high activity but a lower capacity for producing coke than the catalyst of the first layer.

20 Claims, No Drawings

DEHYDROGENATION PROCESS

CROSS REFERENCE TO RELATED APPLICATIONS

None

BACKGROUND OF INVENTION

The present invention relates to an improved process for adiabatic, non-oxidative dehydrogenation of hydrocarbons whereby a hydrocarbon feed stream is passed through a catalyst bed containing at least a first layer of a first catalyst and a second layer of a second catalyst, wherein the catalyst of the first layer exhibits high activity, but also a higher capacity to produce coke than the second catalyst, while the catalyst of the second layer also exhibits high activity but a reduced capacity to make coke. Various preparation and/or treatment processes and/or differences in the composition of the catalysts contained in the two layers can cause the differences in capacity of the catalysts to make coke.

Alkane dehydrogenation is a recognized process for the production of a variety of useful hydrocarbon products, such as isobutylene for conversion to MTBE, isooctane and alkylates to supplement and enrich gasolines and propylene for use in the polymer industry. There are several processes recognized for the catalytic dehydrogenation of light alkanes, including the Süd-Chemie HOUDRY® process. The catalysts that are used in these dehydrogenation processes may be manufactured from different materials. For example, the HOUDRY® process normally utilizes chromia-alumina catalysts. While not limited, the process of the present invention is especially designed for use with the HOUDRY® dehydrogenation process.

In the HOUDRY® process, an aliphatic hydrocarbon, such as propane, is passed through a dehydrogenation catalyst bed, which may contain various layers of catalysts, where the hydrocarbon travels from one layer to the next and in the process is dehydrogenated to its complimentary olefin. Because the dehydrogenation reaction is endothermic and the process is adiabatic, the temperature of the catalyst bed decreases during the dehydrogenation cycle. At the same time, paraffin conversion declines until conversion is no longer economical. The hydrocarbon flow is stopped at this point. After a steam purge, the catalyst is subjected to a regeneration cycle in air in order to remove coke that has been deposited on the catalyst. During the regeneration cycle the catalyst bed gains heat, some of which is produced by burning of the coke. Thus, coke combustion plays an important role in the heat balance in the catalyst bed. After regeneration the catalyst is reduced, and the cycle is repeated. This process is discussed in detail, for example in U.S. Pat. Nos. 2,419,997 and 5,510,557 and U.S. patent application Ser. No. 20040087825, which references are incorporated herein by reference.

Due to equilibrium limitations, dehydrogenation processes require relatively high operating temperatures. However, as the temperature is increased, a point is reached where the production of undesirable by-products, such as light gas and coke, is so high that the yield of the desired olefin begins to decline.

Thus, it would be advantageous if a method could be developed for the dehydrogenation of aliphatic hydrocarbons that improves olefin selectivity and yield by optimizing the performance of the catalysts of the catalyst bed, especially for production of coke, by various methods such as by adjusting the composition and/or performance of the catalysts contained in the catalyst bed.

SUMMARY OF THE INVENTION

The present invention provides a method for optimization of the performance of a catalyst bed, especially for use in a dehydrogenation process, comprising loading layers of catalysts into a dehydrogenation catalyst bed, at least two of which exhibit different capacities for production of coke. The composition of the catalyst of each catalyst layer is optimized based on requirements of heat balance and kinetics, which are different depending on the location of the catalysts in the catalyst bed.

The present invention preferably provides a process for the dehydrogenation of aliphatic hydrocarbons including (a) loading at least a first and a second layer of dehydrogenation catalysts into a catalyst bed, whereby the hydrocarbon feed first contacts the catalysts of the first layer, wherein the catalysts of each layer exhibit different, predetermined capacities for the production of coke, (b) reducing the catalysts loaded in the catalyst bed with a reducing gas, such as hydrogen, and evacuating the bed, (c) introducing an aliphatic hydrocarbon feed stream into the catalyst bed, such that the feed stream initially contacts the first layer of the catalyst bed prior to contacting the second layer of the catalyst bed, whereby the aliphatic hydrocarbon is dehydrogenated, (d) steam purging and regenerating the catalysts contained in the catalyst bed, and (e) repeating these steps, whereby the catalysts of the first layer of the catalyst bed have significant activity but also a higher capacity for producing coke than the catalyst of the second layer and whereby the catalysts of the second layer of the catalyst bed may have the same or different activity as that of the catalysts of the first catalyst layer, but have a reduced capacity to make coke.

The different capacities of the catalysts of the different layers to make coke may be achieved by using various processes to produce the catalysts and/or compositions of the catalysts of the two layers. In one embodiment, the composition of the catalyst of the first layer contains a higher percentage of $Cr^{6+}$ components, by weight, than the catalysts of the second layer. In a further embodiment, the surface area of the catalyst of the first layer is greater than that of the catalyst of the second layer. In this embodiment, the surface area of the catalyst of the first layer is greater than 90 $m^2/g$, and preferably greater than 90 $m^2/g$ to about 120 $m^2/g$, while the surface area of the catalyst of the second layer is less than 90 $m^2/g$ and preferably from about 50 $m^2/g$ to less than 90 $m^2/g$. These differences in surface area can be achieved by various processing steps, such as by calcination in varying percentages of steam.

Other processes of manufacture and compositions of the catalysts may be utilized to achieve this difference in coke making capability, all of which are within the scope of this invention, to maintain the high overall activity of the catalysts of both layers while reducing the capacity of the catalyst of the second layer to make coke over the capacity of the catalyst of the first layer.

DETAILED DESCRIPTION OF THE INVENTION

The method of the present invention is intended for use in aliphatic hydrocarbon dehydrogenation reactions, specifically for the production of olefins. These improvements especially apply to HOUDRY® dehydrogenation processes, as described, for example, in U.S. Pat. No. 2,419,997 and U.S.

Pat. No. 5,510,557. The HOUDRY® process includes a series of process steps wherein the catalyst bed is evacuated, reduced with a reducing gas, such as hydrogen, and evacuated. The aliphatic hydrocarbon is then introduced into the catalyst bed and dehydrogenated. The catalyst bed is then steamed, purged and regenerated and the cycle is repeated starting with the reduction cycle. One particularly preferred utilization for these catalysts is for the conversion of propane into propylene. The method of the invention preferably utilizes at least two types of catalysts contained in at least two layers of the catalyst bed.

It has been discovered that an enhanced adiabatic, non-oxidative paraffin dehydrogenation process with improved olefin yield can be achieved if at least two catalysts with different compositions and/or different methods of production are utilized for the catalysts contained within the catalyst bed of the invention, wherein the first catalyst is placed in a first layer of the catalyst bed, through which the feed stream first passes, and the second catalyst is placed in a second layer of the catalyst bed, through which the feed stream passes after passing through the first catalyst layer.

It has been surprisingly discovered that improvements in the dehydrogenation process occur, such as higher olefin selectivity and higher olefin yield, when the catalyst of the first layer has high activity and a higher capacity for the production of coke than the catalyst of the second layer, while the catalyst of the second layer may have the same or a different activity from the catalyst of the first layer, but exhibits a capacity to make coke which is reduced from the capacity of the catalyst of the first layer. In a preferred embodiment, the catalyst in the second layer produces about 20 wt. percent to about 80 wt. percent less coke than the catalyst in the first layer. More than two layers of catalysts may be used, wherein the catalysts of the various layers may have the same or different compositions, methods of production, performances and capacities to make coke. Further, the arrangement of the different catalysts in the catalyst bed can vary as long as the feed stream contacts the catalyst of the first layer prior to contacting the catalyst of the second layer. Without being bound by any particular theory, it is believed that by carefully adjusting the activity and the capacity to produce coke of the different catalysts of the catalyst layers, the current invention optimizes the temperature profile in the catalyst bed and accordingly, optimizes the performance of the catalysts.

In a preferred embodiment, the current invention is optimized when the reduction in coke production of the second layer is at least about 20 wt. percent to about 80 wt. percent, thereby reducing the layers of catalysts with different capacities which are needed. Each catalyst layer can be optimized based on requirements of heat balance and kinetics, which are different depending on the position and quantity of the catalyst in the catalyst bed, and the temperature of the feed stream at a particular layer. This improved dehydrogenation process, in addition to improved olefin selectivity and improved olefin yield, has additional advantages, such as reduced instability problems, which are commonly encountered, and allows the reactor to operate at the highest possible temperature, thereby generating the highest possible conversion while reducing the likelihood of hot spot formation, increasing process selectivity, and yet, still providing stable reactor operations at high conversion rates.

In a preferred embodiment the catalyst of the first layer comprises from 50 to about 85 percent, by weight of the total catalysts in the catalyst bed while the catalyst of the second layer preferably comprises less than 50 percent to about 15 percent of the catalysts, by weight, in the catalyst bed.

Various modifications can be made to the composition and method of production of the catalysts of the first and second layers to achieve the desired process improvements, all of which are within the scope of the invention. For example, in one embodiment, both catalysts comprise from about 70 to about 90% of an alumina carrier, preferably an eta alumina carrier, and from about 10 to about 30% by weight of one or more chromium compounds. To reduce the capacity of the catalyst of the second layer to make coke, the quantity of $Cr^{+6}$ cations in the catalyst of the second layer is less than is present in the catalyst in the first layer. In one preferred embodiment, the catalyst of the first layer comprises greater than 1.1% by weight, preferably at least about 1.2% by weight, and more preferably at least about 1.5% by weight of chromium compounds containing $Cr^{+6}$ cations, while the catalyst of the second layer contains chromium compounds with $Cr^{+6}$ cations in a quantity less than 1.1% by weight, preferably from about 0.01 to less than 1.1% by weight.

Alternatively, the catalyst of first layer can be produced by adding an alkali metal compound, preferably a sodium component, to the catalyst of the first layer in an amount less than the amount added to the catalyst of the second layer. In one preferred embodiment, the amount of the alkali metal compound, preferably a sodium compound, that is added to the second layer is at least 0.5 to about 0.7%, by weight, calculated as $Na_2O$, while the amount added to the first layer is decreased, containing up to a level of less than 0.5%, by weight, and preferably up to a level less than 0.4%, by weight, calculated as $Na_2O$. If alkali metal compounds other than sodium compounds are used, equivalent molar quantities are used to the quantities of sodium compounds described above.

In another preferred composition, which results in the catalyst of the second layer producing less coke than the catalyst of the first layer, the surface area of the catalyst of the second layer is less than that of the catalyst of the first layer. In a preferred embodiment the surface area of the catalyst of the first layer is at least 90 $m^2/g$, and preferably greater than 90 to about 120 $m^2/g$, while the surface area of the catalyst of the second layer is less than 90 $m^2/g$, preferably about 50 to less than 90 $m^2/g$, most preferably about 80 to less than 90 $m^2/g$.

In another preferred process, the pore size distribution of the catalyst of first and second layers is adjusted so that the catalyst of the first layer produces more coke than the catalyst of the second layer. Preferably, this is achieved by the catalyst of the first layer having smaller pores, on average, than the catalyst of the second layer.

Another processing step to produce the catalyst of the second layer with a reduced capacity to make coke is by calcination of the catalyst of the second layer in a steam/air atmosphere with a steam concentration preferably in an amount greater than 20% to 100% by volume, and preferably about 80-100% by volume. In an alternative process or a process to be used in conjunction with this process, the catalyst of the first layer can be calcined in a steam/air atmosphere with added steam in an amount up to no more than 20% by volume, and more preferably in an atmosphere without any added steam.

Another modification to the composition of the catalyst of the first layer which can increase its capacity to produce coke over the capacity of the catalyst of the second layer is by the addition of Ni compounds, preferably in an amount from about 0.5 to about 1.7% by weight, calculated as NiO, or by adding Pt compounds in an amount from 100 ppm to about 10,000 ppm by weight.

Other modifications to the composition or process of production of the catalysts of the two layers, which are known to those skilled in the art, can also be used to assure that the catalyst of the second layer produces coke in an amount less than is produced by the catalyst of the first layer.

To improve the overall performance of the catalysts of both the first and the second layer, they may include additional components which enhance their activity or stability, such as zirconium compounds, preferably zirconium oxide, in an amount of about 0.1 to about 5% by weight and preferably from about 0.1 to about 1% by weight, calculated as $ZrO_2$, and/or magnesium compounds, preferably magnesium oxide, in an amount of about 0.1 to about 5% by weight, and preferably from about 0.1 to about 1% by weight, calculated as MgO.

Other additives may also be added to either or both of the catalysts of the catalyst bed, such as silica, cerium compounds and other additives in an amount of about 0.1 to about 5%, preferably from about 0.1 to about 1%, by weight.

Further, inert materials may be substituted for the active catalyst of either or both of the first and second layers in the catalyst beds.

The present invention is also a method of dehydrogenating a hydrocarbon feed stream, particularly a feed stream containing C3 to C5 aliphatic hydrocarbons, such as propane, using the catalysts of the invention. In this process, catalysts of different composition, or produced by different processes, are loaded within at least a first and second layer within a catalyst bed within a reactor. The hot catalyst bed is evacuated and the catalysts are then reduced using a reducing gas, such as hydrogen, and evacuated again. An aliphatic hydrocarbon is then fed into the catalyst bed as part of a gas feed at a preselected flow rate, such that the feed stream initially contacts the catalyst of the first layer and then the catalyst of the second layer. Following dehydrogenation, the catalyst bed is steam purged, regenerated and reduced. Following reduction, the process steps can be repeated with the feed stream again.

The current process provides optimization of the performance of the catalyst bed by utilization of two different catalysts with different capacities to produce coke in different layers within the catalyst bed. Without being bound by any particular theory, it is believed that each catalyst layer optimizes performance based on the requirements of heat balance and kinetics. The improved process reduces instability, allows the reactor to operate at a high reaction temperature resulting in high conversion yet high selectivity while enhancing the stability of the reactor.

It will be apparent from the foregoing that while particular forms of the invention have been illustrated, various modifications can be made without departing from the invention.

The invention claimed is:

1. A process for the dehydrogenation of aliphatic hydrocarbons, comprising (a) loading a first dehydrogenation catalyst in a first layer of a catalyst bed in a reactor; (b) loading a second dehydrogenation catalyst in a second layer of the catalyst bed in the reactor; (c) reducing the catalysts; and (d) introducing a feed stream to the catalyst bed, comprising an aliphatic hydrocarbon, such that the feed stream initially contacts the catalyst in the first catalyst layer and then the catalyst in the second catalyst layer, wherein the first catalyst comprises a catalyst with high activity but a higher capacity for producing coke than the catalyst of the second layer, and the second catalyst comprises a catalyst with the same or different activity, but a reduced capacity to make coke from the capacity of the catalyst of the first layer, wherein the composition of the catalysts of the first and second layers comprises from about 70 to about 90% by weight of alumina and from about 10 to about 30% by weight of one or more chromium compounds, and wherein the composition of the catalysts of the first layer contains a higher percentage of $Cr^{+6}$ components, by weight, than the catalysts of the second layer.

2. The process of claim 1, wherein the catalyst of the second layer produces about 20 to about 80% by weight less coke than the catalyst in the first layer.

3. The process of claim 1, wherein the chromium compounds of the catalysts of the first layer comprise at least about 1.2% of a $Cr^{6+}$ composition, by weight.

4. The process of claim 1, wherein the chromium compounds of the catalysts of the second layer comprise from about 0.01 to less than 1.1% by weight $Cr^{6+}$ compounds, based on the total weight of the catalyst.

5. The process of claim 1, wherein the composition of the catalyst of the second layer further comprises at least 0.5 to about 0.7% of $Na_2O$ by weight.

6. The process of claim 5, wherein the composition of the catalyst of the second layer, instead of including at least 0.5 to about 0.7 weight percent of $Na_2O$, instead comprises another alkali metal compound on an equivalent molar basis.

7. The process of claim 1, wherein the composition of the catalyst of the first layer further comprises from about 0.5 to about 1.7% by weight of a nickel compound, calculated as NiO.

8. The process of claim 1, wherein the composition of the catalyst of the first layer further comprises from about 100 ppm to about 10,000 ppm of a Pt compound.

9. The process of claim 1, wherein the composition of the catalyst of the first layer further comprises less than 0.5% by weight of $Na^2O$.

10. The process of claim 9, wherein the composition of the catalyst of the first layer, instead of including less than 0.5% by weight $Na_2 0$, instead comprises another alkali metal compound on an equivalent molar basis.

11. The process of claim 1, wherein the surface area of the catalyst of the first layer is greater than the surface area of the catalyst of the second layer.

12. The process of claim 1, wherein the surface area of the catalyst of the first layer is at least 90 $m^2/g$.

13. The process of claim 1, wherein the surface area of the catalyst of the first layer is greater than 90 $m^2/g$ to about 120 $m^2/g$.

14. The process of claim 1, wherein the surface area of the catalyst of the second layer is from about 50 $m^2/g$ to 90 $m^2/g$.

15. The process of claim 1, wherein the catalyst of the first layer comprises from about 85% to 50% by weight of the catalysts in the reactor.

16. The process of claim 1, wherein the catalyst of the second layer comprises from about 15% to less than 50% by weight of the catalysts in the reactor.

17. The process of claim 1, wherein the catalyst of the first layer is calcined in a steam/air atmosphere with a steam concentration no more than 20% by volume of added steam.

18. The process of claim 1, wherein the catalyst of the second layer is calcined in a steam/air atmosphere with a steam concentration greater than 20 to 100% by volume of added steam.

19. The process of claim 1, wherein the catalyst of the second layer is calcined in a steam/air atmosphere with a steam concentration from about 80 to 100% by volume of added steam.

20. The process of claim 1, wherein the average pore size of the pores on the catalyst of the first layer is smaller than the average pore size of the pores on the catalyst of the second layer.

* * * * *